(12) United States Patent
Roesch et al.

(10) Patent No.: US 9,969,666 B1
(45) Date of Patent: May 15, 2018

(54) METHOD AND APPARATUS FOR CO-PRODUCTION OF METHANOL AND HYDROGEN

(71) Applicant: L'Air Liquide, Société Anonyme pour l'Etude et l'Exploitation des Procédés Georges Claude, Paris (FR)

(72) Inventors: Alexander Roesch, Katy, TX (US); Alain Guillard, Houston, TX (US); Frank Castillo-Welter, Frankfurt am Main (DE); Timm P. Schuhmann, Offenbach (DE); Teja Schmid McGuinness, Frankfurt am Main (DE); Tobias Oelmann, Frankfurt am Main (DE)

(73) Assignee: L'Air Liquide Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days. days.

(21) Appl. No.: 15/637,189

(22) Filed: Jun. 29, 2017

Related U.S. Application Data

(60) Provisional application No. 62/470,420, filed on Mar. 13, 2017.

(51) Int. Cl.
| | |
|---|---|
| *C07C 29/151* | (2006.01) |
| *C07C 31/04* | (2006.01) |
| *C01B 3/12* | (2006.01) |
| *B01D 3/14* | (2006.01) |
| *B01D 53/047* | (2006.01) |

(Continued)

(52) U.S. Cl.
CPC ............ *C07C 29/1518* (2013.01); *B01D 3/14* (2013.01); *B01D 53/047* (2013.01); *C01B 3/12* (2013.01); *C07C 31/04* (2013.01); *F25B 1/00* (2013.01); *F28B 1/00* (2013.01)

(58) Field of Classification Search
CPC .... C01B 3/38; C01B 3/48; C01B 3/24; C01B 2203/0233; C01B 2203/025; C01B 2203/0288; C01B 2203/043; C01B 2203/0495; C01B 2203/061; C01B 2203/0816; C01B 2203/0827; C01B 2203/0838; C01B 2203/0844; C01B 2203/0146; C01B 2203/0148; C07C 29/1518; C07C 31/04
See application file for complete search history.

(56) References Cited

U.S. PATENT DOCUMENTS 6,214,314 B1 * 4/2001 Abbott ...................... C01B 3/38
423/650
6,486,219 B1 * 11/2002 Janda ...................... C01B 3/382
518/700

(Continued)

*Primary Examiner* — Jafar Parsa
(74) *Attorney, Agent, or Firm* — Elwood L. Haynes

(57) ABSTRACT

A method for the co-production of hydrogen and crude methanol, including; a hydrocarbon processing reforming or gasification process generating a syngas stream comprising hydrogen, carbon monoxide and carbon dioxide; introducing at least a portion of the syngas stream to a once-through methanol synthesis reactor: introducing at least a portion of the stream from methanol reactor to a separation device separating this stream into a crude methanol stream and methanol synthesis off gas stream; introducing at least a portion of the methanol synthesis off gas to a hydrogen separation device, thereby producing a pure hydrogen stream.

17 Claims, 5 Drawing Sheets

(51) Int. Cl.
*F25B 1/00* (2006.01)
*F28B 1/00* (2006.01)

(56) References Cited

U.S. PATENT DOCUMENTS

| | | | |
|---|---|---|---|
| 6,706,770 B2 | 3/2004 | Patel et al. | |
| 2003/0191196 A1* | 10/2003 | Madhubhai | C01B 3/48 |
| | | | 518/704 |
| 2013/0095029 A1* | 4/2013 | Han | C01B 3/025 |
| | | | 423/359 |

* cited by examiner

METHOD AND APPARATUS FOR CO-PRODUCTION OF METHANOL AND HYDROGEN

CROSS REFERENCE TO RELATED APPLICATION

This application claims the benefit of priority under 35 U.S.C. § 119 (a) and (b) to U.S. Patent Application No. 62/470,420 filed Mar. 13, 2017, the entire contents of which are incorporated herein by reference.

BACKGROUND

A significant portion of the world's methanol is produced by the catalytic reaction of synthesis gas obtained by reforming hydrocarbons. The synthesis gas may be produced in a steam reformer, an autothermal reformer, or a partial oxidation reformer containing hydrogen, carbon monoxide, and carbon dioxide.

The majority of hydrogen is produced from a synthesis gas produced by the mentioned reforming technologies. For hydrogen production the hydrogen content in the syngas shall be as high as possible whereas for methanol production a suitable synthesis gas composition may be characterized by a hydrogen-carbon oxide molar ratio defined as:

$$\frac{[H_2] - [CO_2]}{[CO] + [CO_2]}$$

where $[H_2]$, $[CO]$, and $[CO_2]$ are the mole fractions of the respective components in the synthesis gas.

The methanol production typically takes place at location where the hydrocarbon feedstock e.g. natural gas is available at low cost e.g. Trinidad. The methanol is then stored and transported on a global basis to its consumers. Compared to methanol hydrogen as a gaseous product cannot be transported economically over long distances and therefore is typically produced at the location where the H2 product is also consumed e.g. refineries or chemical complexes. However certain refineries or chemical complexes also have a demand for methanol. For those instances a co-production of methanol inside the hydrogen production plant can reduce the production cost, logistics cost and also reduce or eliminated emissions of criteria pollutant generated during the transportation of methanol e.g. shipping via tankers.

FIG. 1 illustrates a typical synthesis gas (syngas) plant for hydrogen production as known to the art. A light hydrocarbon, natural gas in this example, is fed into a reformer. A steam methane reformer is indicated in FIG. 1, but the above discussed processes apply equally wed, depending on the type of feedstock, desired ratio of carbon monoxide, carbon dioxide and hydrogen. Depending on the available natural gas supply pressure, a natural gas feed compressor may be needed. As the syngas is generated at a very high temperature, this gas stream may be cooled in a process gas boiler, thereby producing steam which may be useful elsewhere and thus improving the thermal efficiency of the facility.

If additional hydrogen is desired, a water gas shift reactor may be utilized. Any additional useful heat in the shifted syngas stream may then be extracted in a syngas waste heat recovery unit. As high purity hydrogen is often the desired product from such a system, a hydrogen separation device, a pressure swing adsorption unit in FIG. 1, may be used to separate the hydrogen for export.

FIG. 2 illustrates a combined hydrogen and methanol production facility as known to the art. (see U.S. Pat. No. 6,706,770 for example) A light hydrocarbon, natural gas in this example, is fed into a reformer. A steam methane reformer is indicated in FIG. 2, but the above discussed processes apply equally well, depending on the type of fuel, desired ratio of carbon dioxide and hydrogen, etc. Depending on the available natural gas supply pressure, a feed compressor may be needed. As the syngas is generated at a very high temperature, this gas stream may be cooled in a process gas boiler, thereby producing steam which may be useful elsewhere and thus improving the thermal efficiency of the facility.

In the process scheme of FIG. 2, the cooled syngas is split into a first stream that is combined with process steam and enters the shift reactor (as discussed above). Then into a waste heat recovery unit, and then a hydrogen separation device, such as a pressure swing adsorption unit, to produce hydrogen for downstream use. The cooled syngas is split into a second stream that enters a second waste heat recovery unit, then is compressed and then introduced into a methanol reactor, thus producing a crude methanol stream for use downstream.

In order to utilize the synthesis gas most efficiently in the above reactions, stoichiometric amounts of hydrogen and carbon oxides are preferred. Synthesis gas with a suitable stoichiometric composition for methanol production has a value of the hydrogen-carbon oxide molar ratio of 2.0-2.4. Methanol is produced by reacting the synthesis gas catalytically in a pressurized reactor to yield methanol and unreacted synthesis gas, the methanol is condensed and separated from the unreacted synthesis gas, and a portion of the unreacted synthesis gas is recycled to the reactor feed to increase overall conversion. A certain percentage of the unreacted synthesis gas must be purged from the methanol reactor loop so that components who may be present the synthesis gas but not participating in the methanol synthesis e.g. N2 and CH4, Ar do not build up in the reactor feed gas.

Synthesis gas produced by steam reforming of light hydrocarbons generally contains excess hydrogen when used for methanol production. Thus while purging inert components out of the methanol synthesis loop a significant amount of unreacted hydrogen must be withdrawn and may be used as waste fuel. This purge gas also contains valuable carbon oxides, which become unavailable for conversion to methanol, and this loss adversely affects methanol production economics.

Several approaches to minimize the amount of purge gas or to valorize the purge gas differently have been utilized in commercial methanol production. In one approach, imported carbon dioxide is mixed with either the synthesis gas feed to the methanol reactor or the feed hydrocarbon to the steam reforming step. This gives a methanol reactor feed gas that is closer to the preferred stoichiometric composition, but is possible only when a source of carbon dioxide is readily available. In another approach, unreacted synthesis gas is separated by various methods into a stream enriched in carbon oxides and a stream enriched in hydrogen, the carbon oxide-rich stream is recycled to the reformer or the methanol reactor, and the hydrogen-enriched stream is used for fuel. Membrane systems, absorption processes, and pressure swing adsorption have been used to effect separation of the unreacted synthesis gas.

An alternative approach is to generate the synthesis gas by methods other than steam reforming wherein these methods produce a synthesis gas closer to the preferred hydrogen-carbon oxide ratio for methanol production. Known methods to generate the preferred synthesis gas composition include the partial oxidation, autothermal reforming, and a two-stage process comprising steam reforming followed by oxygen secondary reforming. These methods all require a supply of oxygen, however, and the capital costs are higher than for simple steam reforming.

There is clearly a need in the industry for a more energy efficient and cost effective system for the co-production of hydrogen and methanol.

SUMMARY

A method for the co-production of hydrogen and crude methanol, including; a hydrocarbon processing reforming or gasification process generating a syngas stream comprising hydrogen, carbon monoxide and carbon dioxide; introducing at least a portion of the syngas stream to a once-through methanol synthesis reactor: introducing at least a portion of the stream from methanol reactor to a separation device separating this stream into a crude methanol stream and methanol synthesis off gas stream; introducing at least a portion of the methanol synthesis off gas to a hydrogen separation device, thereby producing a pure hydrogen stream.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
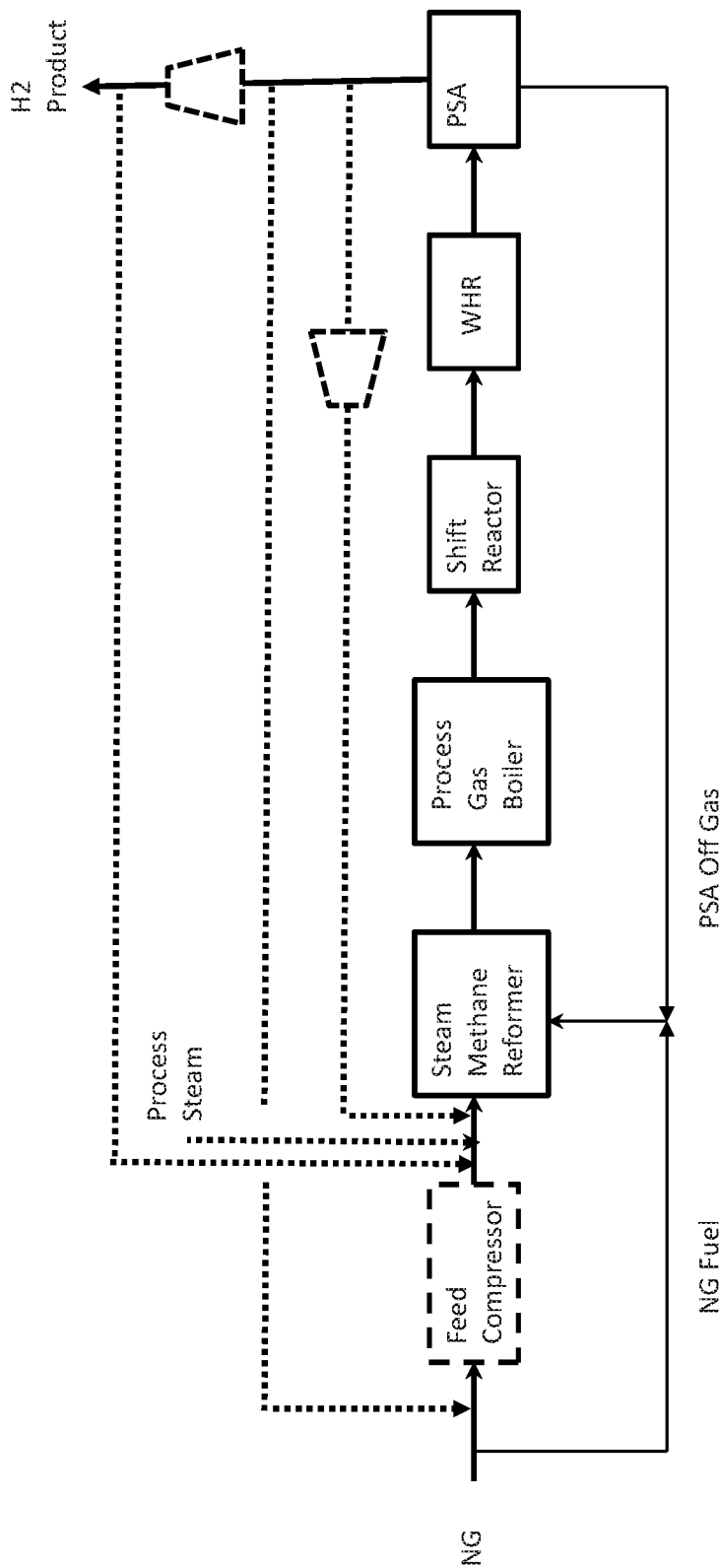
FIG. 1 is a schematic representation a typical steam methane reformer hydrogen plant, as is known to the art.
Figure 2:
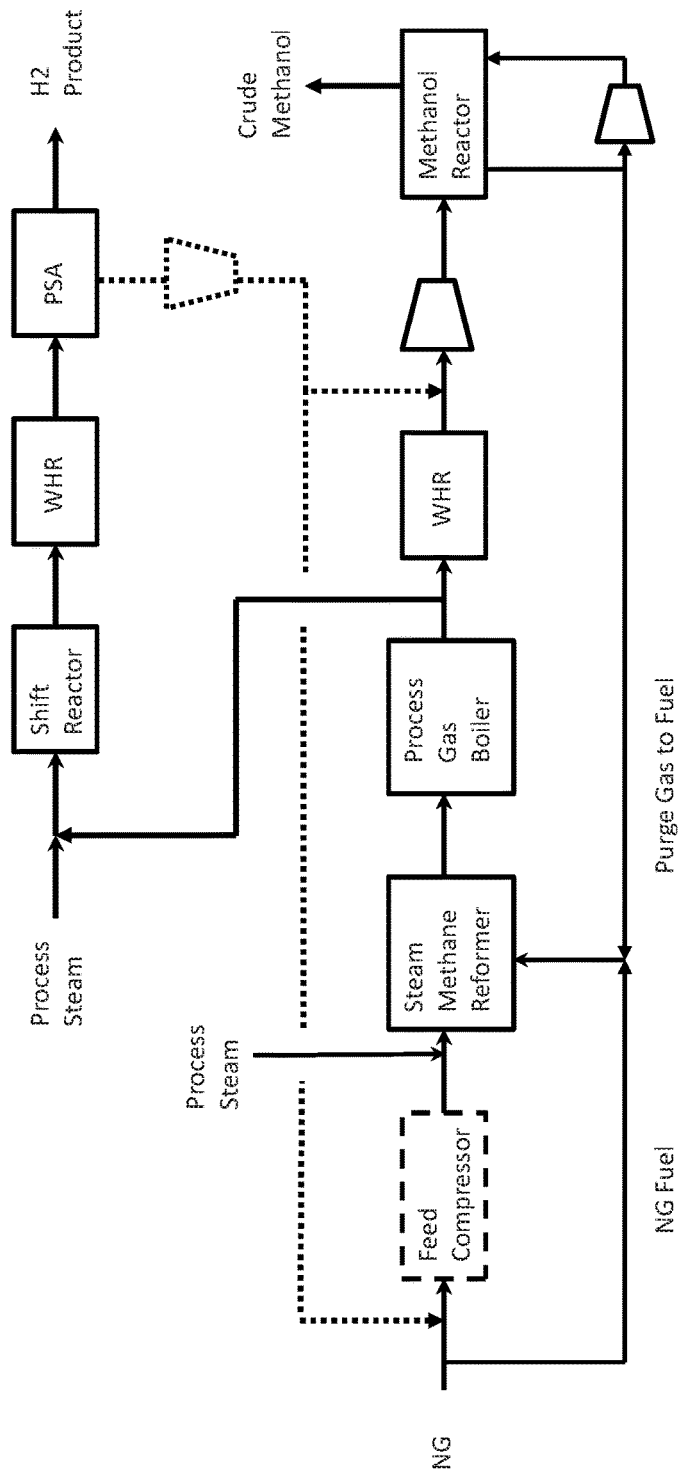
FIG. 2 is a schematic representation of a typical combination of a methanol and hydrogen plant, as is known to the art.

Illustrative embodiments of the invention are described below. While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

Element Numbers

101=hydrocarbon feed stream
102=feed compressor
103=synthesis gas reactor/generator
104=process gas waste heat boiler
105=water gas shift reactor
106=waste heat recovery system
107=hydrogen purification device (e.g. pressure swing adsorption unit (PSA)
108=product hydrogen compressor
109=product hydrogen stream
110=once-through methanol reactor system
110a=once-through methanol reactor
111=methanol purification unit with distillation column
112=Un-reacted syngas containing gaseous methanol
113=Un-reacted syngas containing liquid methanol
114=purified methanol product stream
115=process water from methanol distillation column
116=crude methanol product stream
117=unshifted syngas bypass stream (bypassing the water gas shift reactor)
118=PSA off-gas stream
119=methanol distillation off-gas stream
121=hydrocarbon fuel
123=steam to methanol distillation system
124=syngas to waste heat recovery
125=hydrogen stream to hydrocarbon feed stream
126=methanol synthesis off gas stream to PSA
127=steam to synthesis gas generation process
128=high purity hydrogen stream
129=steam export stream to the overall plant steam system
130=condensate stream
131=water stream to water gas shift reactor (optionally)
150=gas-liquid separator device for extraction of process condensate from syngas
151=gas-liquid separation device for extraction of crude methanol
160=heat exchanger for syngas heating (e.g. interchanger)
161=hot, wet syngas stream (prior to gas-liquid separator)
162=pre-heated syngas stream (after the gas-liquid separator)
163=heated syngas stream 171=gaseous syngas stream
172=syngas compressor
173=steam import from overall plant steam system to methanol distillation system
174=bypass stream around methanol reactor system
200=heat exchanger in syngas cooling section e.g. BFW preheater
201=Cold process stream (e.g. boiler feed water
202=Heated process stream (e.g. heated boiler feed water)
300=Syngas cooler (water or air)
301=Cooling stream
302=Warmed cooling stream
310=interchanger
320=Methanol synthesis gas cooler (water or air)

It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

As used herein, the term "once-through methanol reactor" is defined as a low pressure reactor, where there is no recycling of gas within the methanol reactor. A non-limiting example would be where the methanol reactor comprises a single adiabatic bed or two adiabatic beds with inter-cooling. Typically, such once-through methanol reactors have a conversion rate of less than 20%, or between 10% and 15%, or about 12%.

This invention relates to a method for the co-production of methanol and hydrogen from synthesis gas obtained by reforming light hydrocarbons. In one embodiment, the current invention addresses revamping an existing hydrogen plant, with a focus on avoiding any unnecessary extra equipment and minimizing process impact on the existing hydrogen plant (for example fewer tie-in points) thus making retrofitting an existing plant easier and less expensive. In another embodiment, the present invention may be applied to a new plant to co-produce hydrogen and methanol. Another advantage of the instant process is that it requires only one waste heat recovery/cooling, thus requiring less capital expenditure.

Figure 3:
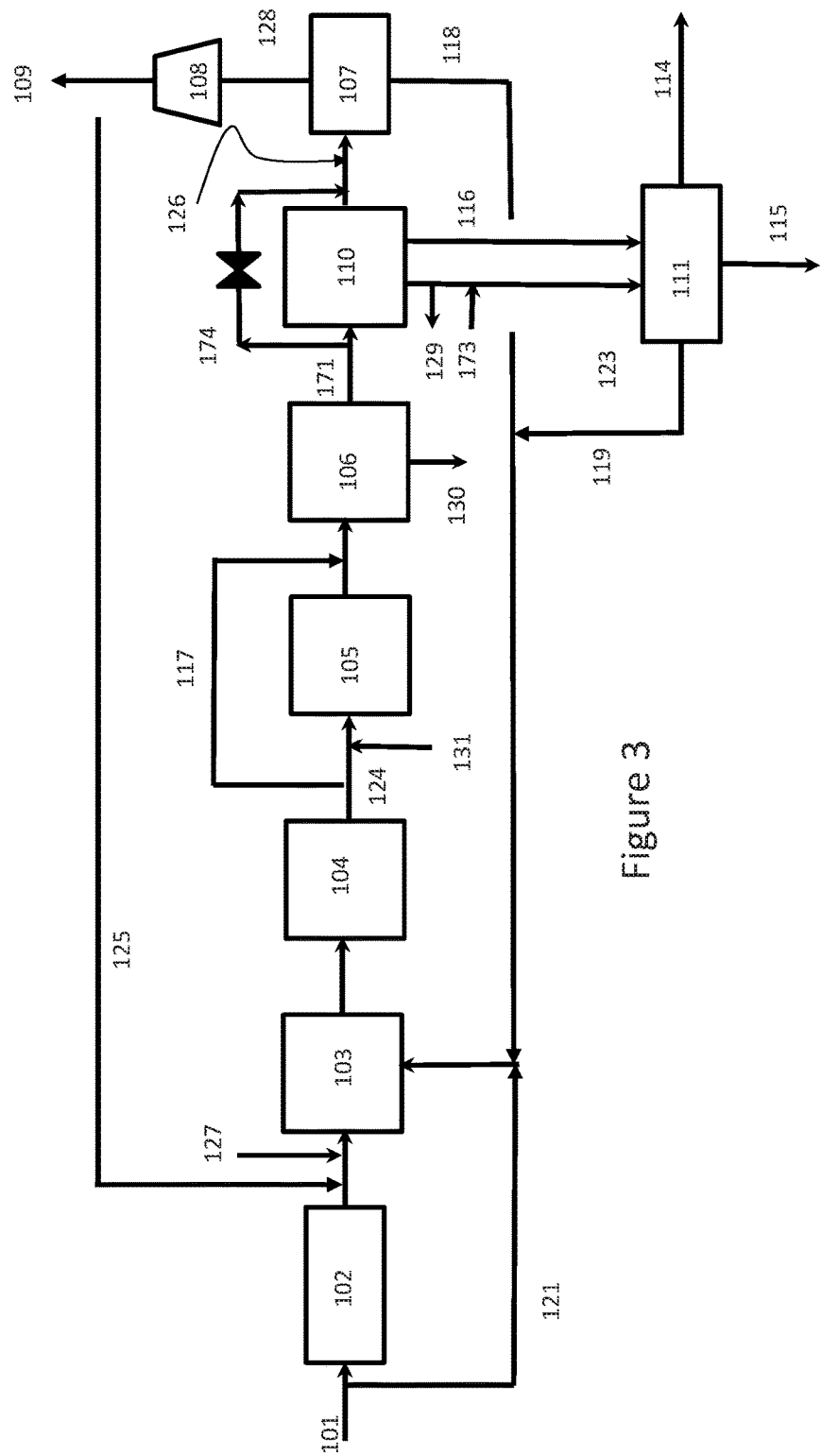
FIG. 3 is a schematic representation of a combined methanol and hydrogen plant without syngas compression prior to admission into the methanol reactor, in accordance with one embodiment of the present invention.
Figure 4:
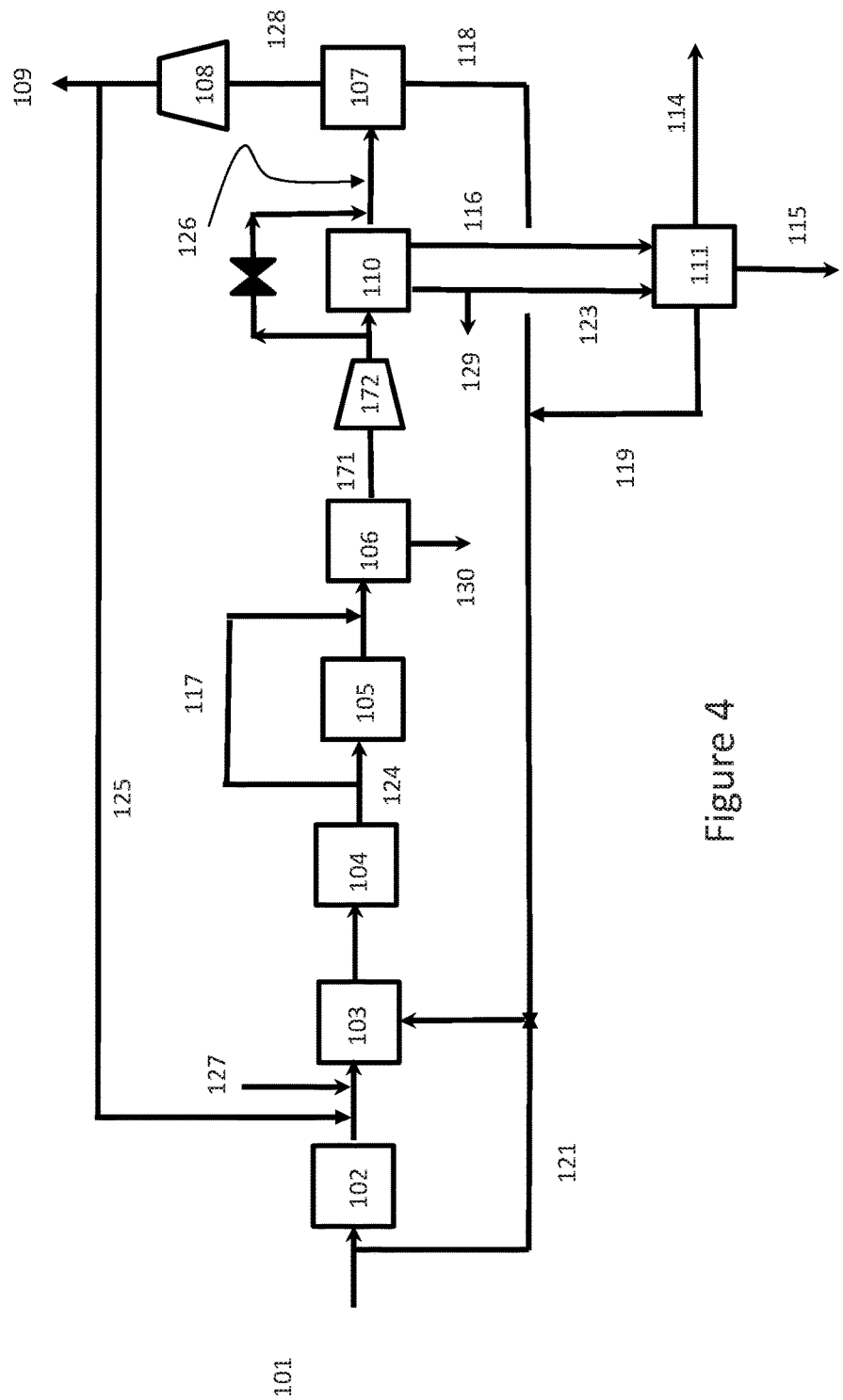
FIG. 4 is a schematic representation of a combined methanol and hydrogen plant with syngas compression prior to admission into the methanol reactor, in accordance with one embodiment of the present invention.
Figure 5:
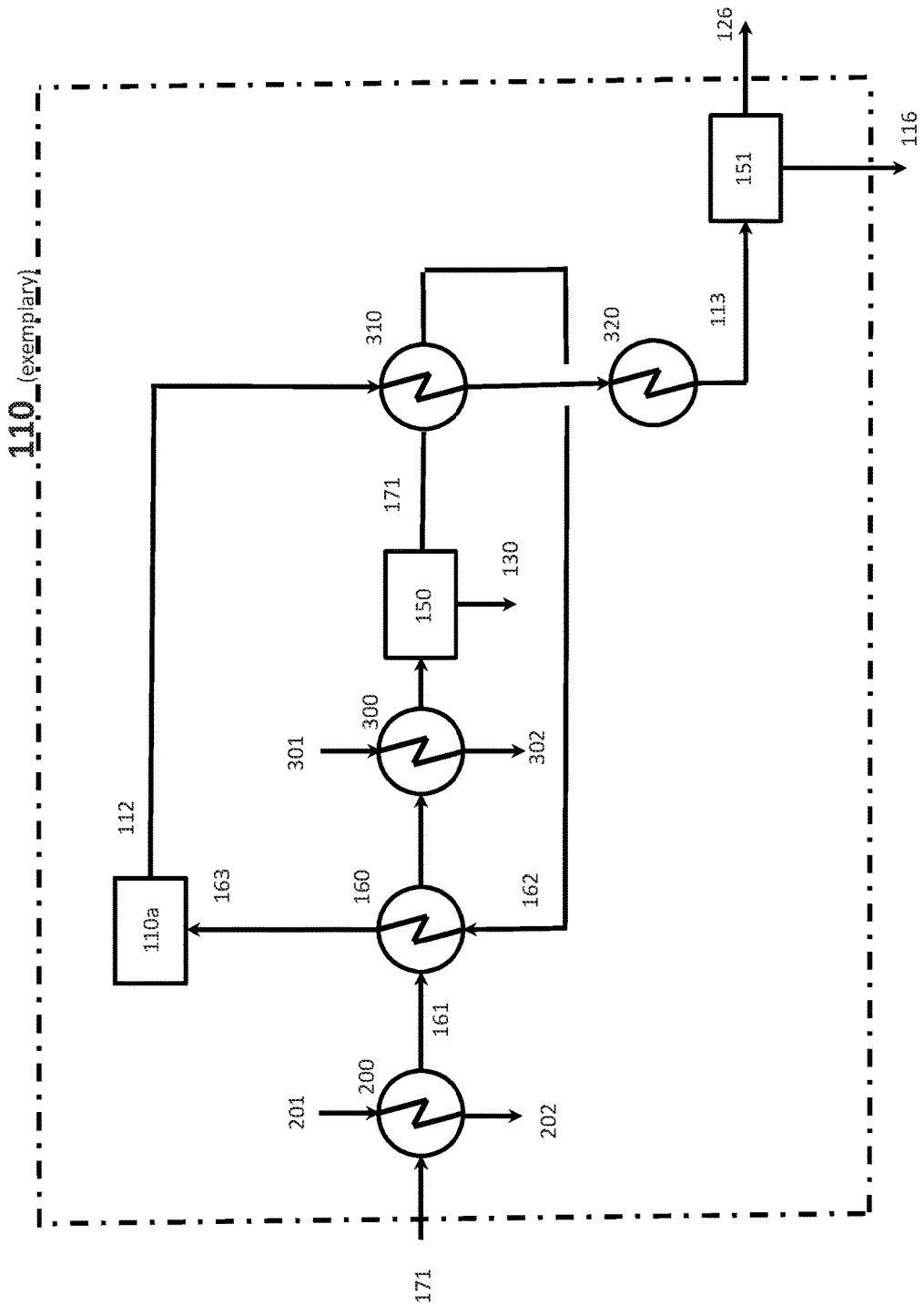
FIG. 5 is a schematic representation indicating details of the methanol reactor system, in accordance with one embodiment of the present invention.

Referring now to FIGS. 3 and 4, one embodiment of the present invention is illustrated. A hydrocarbon feed stream 101 is introduced into synthesis gas (syngas) reactor 103. The hydrocarbon feed stream 101 may be natural gas. The syngas reactor 103 may be a methane reformer (SMR), an autothermal reformer (ATR), or a partial oxidation reformer (POX) or a combination of any of the possible reactor systems. If necessary, hydrocarbon stream 101 may need an increase in downstream pressure, in which case feed compressor 102 may be required. If necessary, steam stream 127 may be introduced into syngas reactor 103. Syngas reactor 103 thus produces a synthesis gas that contains hydrogen, CO, CO2 and other impurities.

The syngas that exits the syngas reactor 103 is typically between 1400° F. and 3000° F., therefore process waste gas heat boiler 104 is used to recover heat from the hot process gas. The cooled syngas may then be introduced into water gas shift reactor 105 in order to convert some of the CO to hydrogen and CO2. An H2O stream 131 might be introduced upstream the shift reactor 105. Shift reactor 105 may be a high temperature shift, a medium temperature shift, a low temperature shift or a combination. As used herein, the term "low temperature shift" refers to a water gas shift conversion reaction that operates at a temperature between about 350° F. and 500° F. As used herein, the term "medium temperature shift" refers to a water gas shift conversion reaction that operates at a temperature between about 400° F. and 675° F. As used herein, the term "high temperature shift" refers to a water gas shift conversion reaction that operates at a temperature between about 600° F. and 950° F. A bypass 117 around shift reactor 105 may be added to adjust the synthesis gas composition to a more suitable composition for producing methanol.

The syngas may then enter an additional steam boiler system; boiler feed water preheater 200 heating a cold BFW 201 to a warm BFW stream 202 or any other type of heat exchanger to recover the sensible heat from the syngas. Prior entering the gas-liquid separator a final cooling step using air cooler or cooling water cooler is typically foreseen.

The additional cooling section may vary depending on the overall plant heat integration and is represented by the unit 106. In FIG. 4, additional cooling is indicated by interchanger 160, which cools hot, wet incoming syngas stream 161 by exchanging heat with pre-heated syngas stream 162 from which liquid has been separated in gas-liquid separator 150. If needed, additional cooling may be provided by syngas cooler 300, which transfers heat to cooling stream 301, thereby producing warmed cooling stream 302. When at the proper temperature, the cooled, syngas stream is then sent to a gas-liquid separator 150 where condensed water is separated from the syngas. The condensate stream 130 can be reused as boiler feed water or disposed to a water treatment unit. The gaseous syngas stream 171 is then sent to once-through methanol reactor 110a. In one embodiment of the present invention, the gaseous syngas stream 171 is compressed prior to entering once-through methanol reactor system 110. Prior entering once-through methanol reactor 110 the syngas stream 171 may be reheated by interchanging heat by mean of heat exchanger 310 with the gas stream 112 coming from once-through methanol reactor 110a. Further heating may be provided for example by heat recovery from hot syngas by using heat exchanger 160, as discussed above.

Prior separating the methanol from the methanol synthesis gas further cooling may be provided by means of methanol synthesis gas cooler 320 (cooling water or air used for cooling). Thus the contained methanol and water in the methanol synthesis gas is condensed and may be separated in gas-liquid separation device 151. The separated crude methanol stream 116 is routed to the methanol purification unit 111 to make high purity methanol stream 114 as a product. The off gas 119 from the methanol purification (with distillation column) 111 may also sent back to synthesis gas reactor 103 to be used as a fuel or feedstock.

The synthesis gas stream 126 from separator 151 is routed to the hydrogen purification device 107. In the hydrogen purification device a hydrogen stream 128 and off gas stream 118 are produced. The off gas 118 from the PSA 107 may be sent back to synthesis gas reactor 103 to be used as a fuel or feedstock. The high purity hydrogen 128 may be compressed 108 and exported as a product hydrogen stream 109, a portion 125 of the hydrogen may be sent back to the hydrocarbon feed stream. A portion of this hydrogen may be used in a hydrodesulfurization (HDS) reactor (not shown) to remove sulfur from natural gas if necessary.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for the co-production of hydrogen and crude methanol, comprising; a hydrocarbon processing reforming or gasification process generating a syngas stream comprising hydrogen, carbon monoxide and carbon dioxide; introducing at least a portion of the syngas stream to a once-through methanol synthesis reactor: introducing at least a portion of the stream from methanol reactor to a separation device separating this stream into a crude methanol stream and methanol synthesis off gas stream; introducing at least a portion of the methanol synthesis off gas to a hydrogen separation device, thereby producing a pure hydrogen stream, wherein at least a fraction of the syngas stream undergoes a water gas shift reaction prior to introduction into the once-through methanol synthesis reactor.

2. The method of claim 1, further comprising introducing the crude methanol stream into a methanol distillation device, thereby producing a pure methanol stream.

3. The method of claim 1, wherein the at least a portion of the syngas stream is introduced into the once-through methanol synthesis reactor without prior compression of the syngas.

4. The method of claim 1, wherein at least a portion of the syngas stream is introduced into the once-through methanol synthesis reactor after compression of the syngas.

5. The method of claim 2, wherein the hydrocarbon processing reforming or gasification process generating a syngas stream comprises a fuel gas stream, and wherein at least a portion of the methanol distillation off-gas stream is returned to the fuel gas stream.

6. The method of claim 2, wherein the hydrocarbon processing reforming or gasification process generating a syngas stream comprises a process feed stream, and wherein at least a portion of the methanol distillation off-gas stream is returned to the process feed stream.

7. The method of claim 1, wherein the hydrogen separation device is a pressure swing adsorption unit.

8. The method of claim 1, wherein the hydrogen separation device is a membrane separation unit.

9. The method of claim 1, where the hydrogen from the hydrogen purification device purifying the methanol synthesis off gas is further compressed by a hydrogen compressor.

10. The method of claim 1, where the synthesis gas generating device is an autothermal reformer or a partial oxidation reactor.

11. The method of claim 1, where the synthesis gas generation device is a steam methane reformer.

12. The method of claim 1, where at least a portion of methanol off gas is utilized as fuel in the steam methane reformer or any other combustion system such as fired process heater or fired steam boilers.

13. The method of claim 1, wherein at least a portion of the produced syngas is bypassing the methanol reactor system and is directly introduced to the hydrogen purification.

14. The method of claim 1, wherein at least a fraction of the methanol synthesis off gas is recycled back to the feed stream of the synthesis gas reactor.

15. The method of claim 1, wherein at least a fraction the methanol synthesis off gas is recycled back to the inlet of the methanol reactor system.

16. The method of claim 1, wherein at least a fraction of the PSA off gas is recycled back to the feed stream of the synthesis gas reactor.

17. The method of claim 1, wherein at least a fraction of the PSA off gas is recycled back to the inlet of the methanol reactor system.

* * * * *